United States Patent [19]
Shirasaki et al.

[11] Patent Number: 4,776,344
[45] Date of Patent: Oct. 11, 1988

[54] ELECTRONIC BLOOD PRESSURE MEASURING DEVICE

[75] Inventors: Osamu Shirasaki, Amagasaki; Satoshi Ueno, Kyoto; Yoshinori Miyawaki, Yawata; Satoshi Egawa, Kyoto, all of Japan

[73] Assignee: Omron Tateisi Electronics Co., Kyoto, Japan

[21] Appl. No.: 833,151

[22] Filed: Feb. 27, 1986

[30] Foreign Application Priority Data

Feb. 28, 1985 [JP] Japan .................................. 60-40753
Mar. 15, 1985 [JP] Japan .................................. 60-52902

[51] Int. Cl.$^4$ .............................................. A61B 5/02
[52] U.S. Cl. ................................ 128/681; 364/413.03
[58] Field of Search .................... 128/677, 679–683; 564/417

[56] References Cited
U.S. PATENT DOCUMENTS 4,105,021 8/1978 Williams et al. .................... 128/683
4,117,835 10/1978 Williams ............................. 128/677
4,461,266 7/1984 Hood, Jr. et al. ................... 128/677

Primary Examiner—Lee S. Cohen
Attorney, Agent, or Firm—Wegner & Bretschneider

[57] ABSTRACT

An electronic blood pressure meter including a cuff, a pressure system for pressurizing and evacuating the cuff, a pressure sensor for detecting the pressure within the cuff, a pulse wave parameter extraction circuit and a blood pressure determining circuit. The pulse wave parameter extraction circuit extracts the maximum level difference in the pulse wave component of the cuff pressure over a certain time intervals and also provides pulse wave maximum and minimum values corresponding to the maximum and minimum values of the pulse wave components over each of the time intervals chosen. The electronic blood pressure meter may also include circuitry for finding maximum and minimum values on each of the higher and lower cuff pressure sides of the cuff and deriving blood pressure measuring readings therefrom.

1 Claim, 18 Drawing Sheets

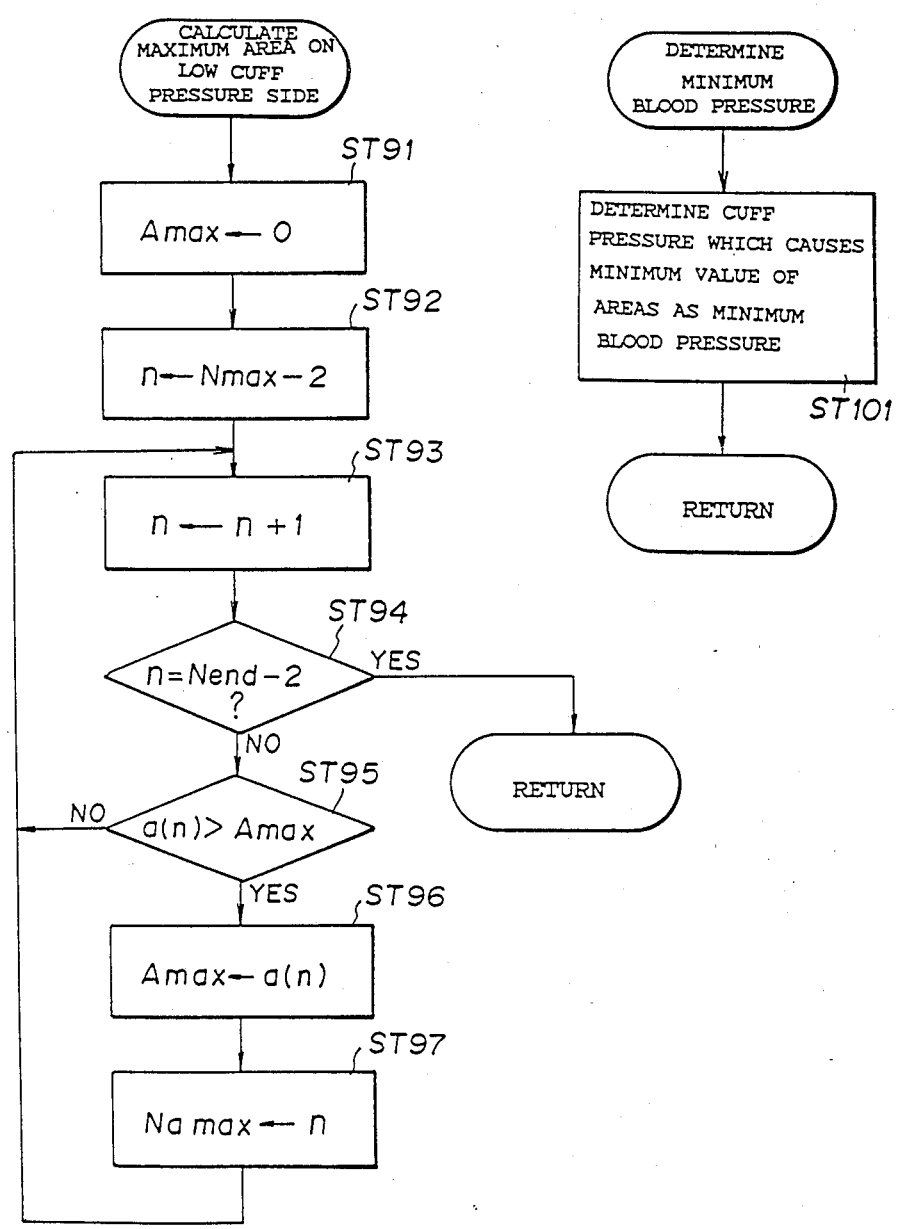

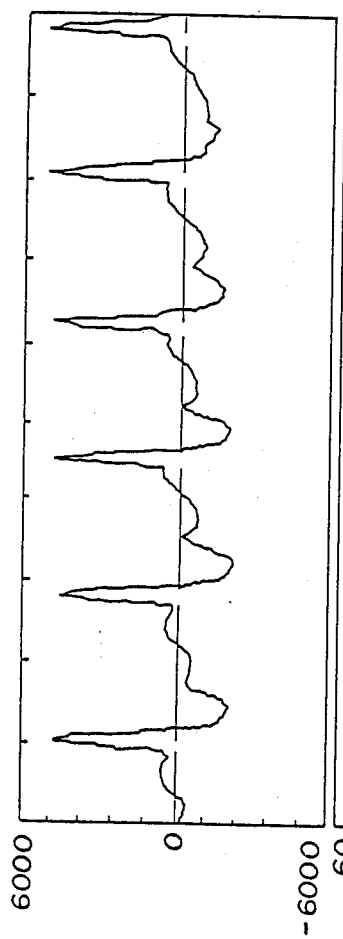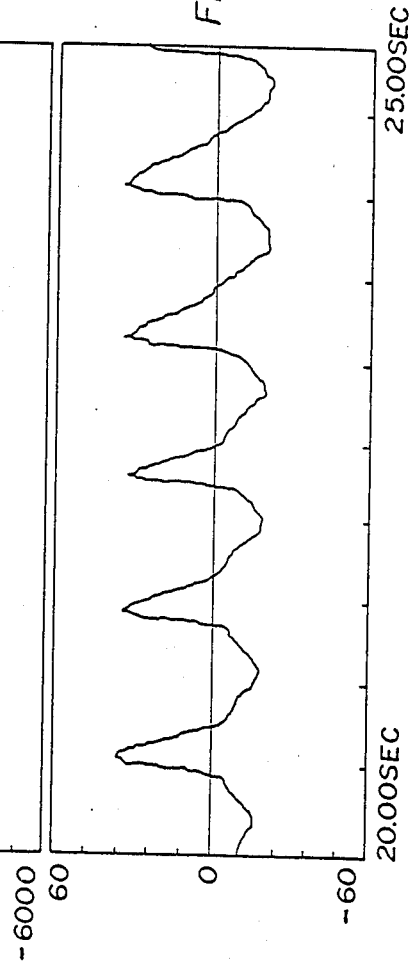
FIG.18(a)
FIG.18(b)

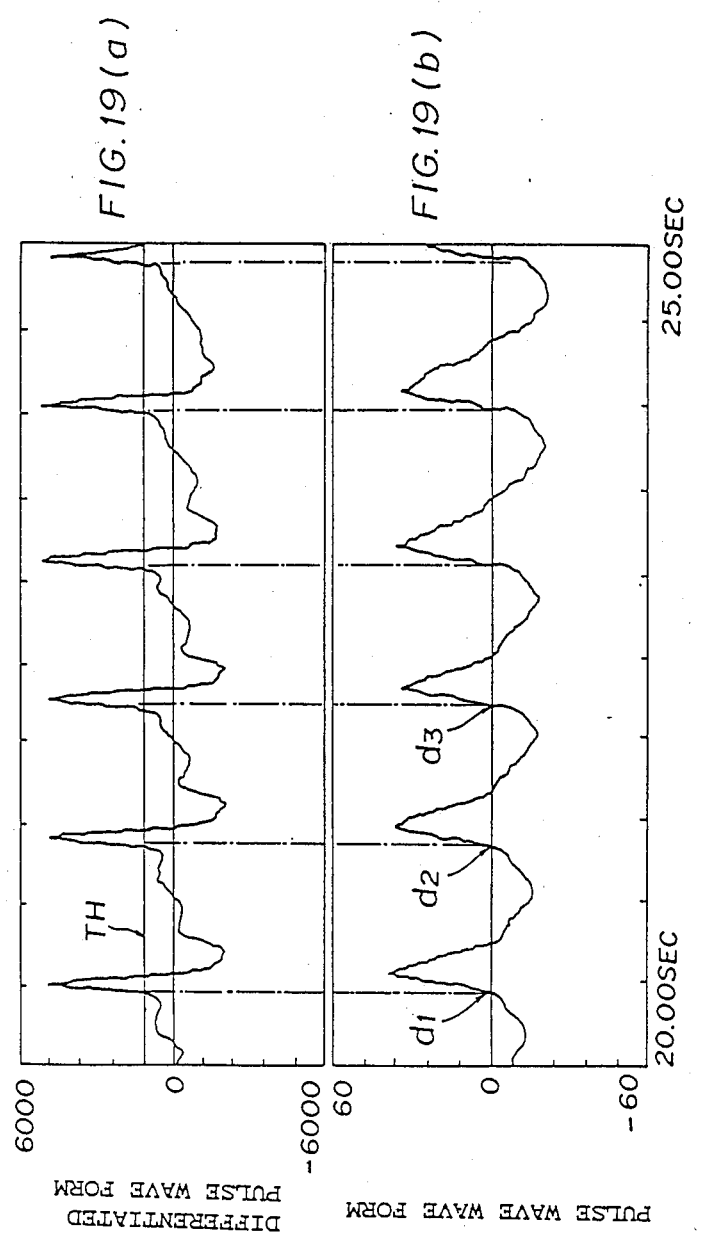

ELECTRONIC BLOOD PRESSURE MEASURING DEVICE

BACKGROUND OF THE INVENTION

The present invention relates to the field of electronic blood pressure measuring devices, and in particular relates to an electronic blood pressure measuring device based upon the oscillation method and to an electronic blood pressure measuring device which measures blood pressure by detecting the amplitude of a pulse wave.

According to a prior art type of electronic blood pressure measuring device based upon the oscillation method, a cuff is wound on the upper arm of the person whose blood pressure is desired to be measured, such as a patient, and, after the cuff is pressurized to a certain pressure level, wave form information is detected from the cuff pressure and a pulse wave component contained in the cuff pressure during the depressurization of the cuff is isolated, so that the average blood pressure, the maximum pressure, and the minimum blood pressure of the person whose blood pressure is being measured may be determined from such data. A typical such electronic blood pressure measuring device detects the DC component in the cuff pressure signal when the cuff is gradually depressurized, as exemplarily shown in FIG. 7a of the accompanying drawings, and derives the level differences between the maximum values and the minimum values of the pulse wave components contained in the cuff pressure signal for each fixed time interval W1, W2, W3 and so on as parameters as shown in FIG. 7b, then arranges these parameters H(1), H(2), H(3), and so on for these time intervals in time sequence as shown in FIG. 7c, and then applies a certain algorithm to the variation curve (envelope line) of these parameters (for instance, by determining the average blood pressure from the cuff pressure of the interval in which the parameter is maximum, the maximum blood pressure from the cuff pressure on the high pressure side corresponding to a parameter which corresponds to 50% of the maximum value, and the minimum blood pressure from the cuff pressure on the low pressure side corresponding to a parameter which corresponds to 70% of the maximum value), so as finally to determine the blood pressure.

In such an electronic blood pressure measuring device, conventionally the cuff pressure associated with each interval is determined as the cuff pressure at the beginning or at the end of the corresponding time interval. However, according to such a conventional electronic blood pressure measuring device, since the cuff pressure corresponding to each time interval is read out from the cuff pressure at the beginning or at the end of the corresponding time interval, the time points at which the pulse wave appears as its maximum value and minimum value in each interval are different from the time point at which the cuff pressure is read, and therefore some error has in the prior art existed between the parameter (maximum level difference) and the cuff pressure, thereby reducing the accuracy of blood pressure determination provided by the device.

Further, since the pressure value corresponding to the parameter is either at the beginning or at the end of the time interval of the cuff pressure signal in which the pulse wave component is combined and therefore the beginning (or the end) of the interval may correspond either to the maximum point of the pulse wave or to the minimum point of the pulse wave depending upon the particular instance, the curve of the cuff pressure signal tends to oscillate within the amplitude of the pulse wave component, whereby some fluctuations exist in the cuff pressure value, and some distortion exists in the curve of the parameter, thereby reducing the accuracy.

Considering another aspect of the present invention, there is a conventionally known blood pressure measuring technology, known as the Riva-Rocci-Korotkoff method has been known as a known blood investigation method. According to an electronic blood pressure measuring device based upon this Riva-Rocci-Korotkoff method, after a cuff is wound around the arm of a patient and the cuff is pressurized for stopping blood flow, as the pressure is reduced gradually, the blood starts flowing and a certain distinctive blood sound (the so called Korotkoff sound) is produced, and then subsequently this sound diminishes as further depressurization of the cuff progressively takes place. The cuff pressure at which the Korotkoff sound is started is then determined as being the maximum blood pressure of the patient, and the cuff pressure at which the Korotkoff sound disappears is determined as being the minimum blood pressure of the patient, in determining the blood pressure of the patient.

As another blood pressure measuring technology, inserting a cannulae into the artery of a patient is known as a blood investigative method.

However, according to an electronic blood pressure measuring device based upon the Riva-Rocci-Korotkoff method among such conventional blood pressure measuring technologies, the obtained Korotkoff sound is a very small signal and its frequency range is from 30 Hz to 150 Hz. Thus, there has been a problem that since this frequency range tends to be affected by external noises and oscillation noises, these noises could become a cause of erroneous detection, and such effects have often caused errors in blood pressure measurements in prior art devices for blood pressure measurement.

And on the other hand, according to a blood pressure measurement based upon a direct method such as introducing a cannulae into a blood vessel of the patient, the pressure of an artery is transmitted to an external blood pressure transducer by way of a cannulae filled with physiological saline, and in such a method the length of the cannulae, mixing of bubbles therein, and zero point drifts of the blood pressure transducers could cause errors in blood pressure measurement. These errors can be reduced by proper handling, but such handling requires skill and care, thus requiring certain hard to provide techniques in carrying out proper blood pressure measurements. Furthermore, such direct methods as described above have the serious disadvantages that such invasive procedures inevitably cause pain, discomfort, and mental strain to the patient, and increase the possibility of blood tube pain and infections.

SUMMARY OF THE INVENTION

Accordingly, it is the primary object of the present invention to provide an electronic blood pressure measuring device, which avoids the above described problems.

In view of such disadvantages of the prior art, a primary object of this invention is to provide a high precision electronic blood pressure measuring device which can produce a proper cuff pressure value corresponding to the time points of extracting the parameter.

It is a further object of the present invention to provide an electronic blood pressure measuring device in which the pulse wave oscillations do not affect the reading of the cuff pressure.

It is a further object of the present invention to provide an electronic blood pressure measuring device which can produce a proper cuff pressure value corresponding to the time points of extracting the parameter.

It is a further object of the present invention to provide an electronic blood pressure measuring device which does not engender pain or discomfort to the patient.

It is a yet further object of the present invention to provide such an electronic blood pressure measuring device, which does not suffer unduly from external noise.

It is a yet further object of the present invention to provide such an electronic blood pressure measuring device, which does not suffer unduly from oscillation noise.

According to one aspect of the present invention, these and other objects are accomplished by an electronic blood pressure meter, comprising: (a) a cuff; (b) a pressure system for pressurizing and evacuating said cuff; (c) a pressure sensor for detecting the pressure within said cuff; (d) a pulse wave parameter extraction means which extracts the maximum level difference in the pulse wave component of the cuff pressure over a certain time interval, for each of a plurality of time intervals; and: (e) a blood pressure determining means for determining a blood pressure according to said cuff pressure and said pulse wave parameter; further comprising: (f) a pulse wave maximum value corresponding cuff pressure extracting means for extracting the cuff pressure corresponding to the maximum value of the pulse wave component over each of said time intervals; (g) a pulse wave minimum value corresponding cuff pressure extracting means for extracting the cuff pressure corresponding to the minimum value of the pulse wave component over each of said time intervals; and: (h) a cuff pressure averaging means for computing an average value of said cuff pressure extracted by said pulse wave maximum value corresponding cuff pressure extracting means and said cuff pressure extracted by said pulse wave minimum value corresponding cuff pressure extracting means; (i) said average value as computed by said cuff pressure averaging means being taken as the cuff pressure of said particular time interval; and, according to another aspect of the present invention, these and other objects are accomplished by an electronic blood pressure meter, comprising: (a) a cuff; (b) a pressure system for pressurizing and evacuating said cuff; (c) a pressure sensor for detecting the pressure within said cuff; (d) a pulse wave sensor for detecting the pulse wave component in the course of cuff pressure changes; (e) a pulse wave amplitude extraction means for extracting the pulse wave amplitude in time sequence; (f) a pulse wave maximum amplitude extraction means for extracting the maximum value of the pulse wave amplitude; (g) an area computing means for computing the area between an envelope line of a certain number of data, including representative data which is extracted in said time sequence, and a line connecting the terminal end data of said data in a sequential manner while shifting the representative data; (h) a first maximum area value extracting means for finding the maximum value of the area computed on the higher cuff pressure side than the cuff pressure corresponding to the maximum value of the amplitude of the pulse wave; (i) a second maximum area value extracting means for finding the maximum value of the area computed on the lower cuff pressure side than the cuff pressure corresponding to the maximum value of the amplitude of the pulse wave; and: (j) a blood pressure determining means for determining a maximum blood pressure from the cuff pressure corresponding to the maximum area extracted by said first maximum area value extracting means, and a minimum blood pressure from the cuff pressure corresponding to the maximum area extracted by said second maximum area value extracting means.

According to the present invention as firstly defined above, in association with the extraction of a parameter for each of the time intervals by each of the extracting means, the cuff pressure which is a maximum value in the interval is extracted by the pulse wave maximum value corresponding cuff pressure extracting means, and the cuff pressure which is a minimum value in the interval is extracted by the pulse wave minimum value corresponding cuff pressure extracting means, and the average value of the cuff pressures at these two time points is calculated by the cuff pressure average value computing means. This average value of the cuff pressures is considered as the cuff pressure of the interval. Therefore, the cuff pressure in each interval is a cuff pressure which is closely related to the time points of extracting the maximum value and the minimum value or the parameters.

On the other hand, according to the present invention as secondly defined above, during the depressurization process after the pressurization of the cuff by the pressure system, the cuff pressure, a pulse wave component, and the pulse wave amplitude are detected. And for each certain number of data of the pulse wave amplitude, the area surrounded by an envelope line of the data and straight lines connecting data are computed in time sequence. And the maximum areas are extracted from the high pressure side and the low pressure side with respect to the cuff pressure corresponding to the maximum amplitude of the pulse wave, and cuff pressures corresponding to the maximum areas extracted on the high pressure side and the low pressure side are determined, so that the maximum blood pressure and the minimum blood pressure can be determined from these cuff pressures. Since the pulse wave component used for determining the blood pressures is extremely low in frequency having a frequency range of 1 Hz to 19 Hz, it is not susceptible to external noises and/or oscillation noises.

BRIEF DESCRIPTION OF THE DRAWINGS

The present invention will now be shown and described with regard to certain of the preferred embodiments thereof, and with reference to the illustrative drawings, which however should not be considered as limitative of the present invention in any way, since the scope of the present invention is to be considered as being deliminated solely by the accompanying claims, rather than by any particular features of the disclosed embodiments or of the drawings. In these drawings:

FIG. 8 is a set of drawings illustration the operation of a second preferred embodiment of the electronic blood pressure measuring device of the present invention.

FIG. 16 is a flow diagram showing in greater detail the control flow of a routine, which is again invoked from said main program, for the computation of the maximum areas on the lower cuff pressure side;

FIG. 17 is a flow diagram showing in greater detail the control flow of a routine, which is yet again invoked from said main program, for the determination of the minimum blood pressure;

FIGS. 18a and b are wave form diagrams for illustrating the differentiated pulse wave wave form and pulse wave wave form of said second preferred embodiment of the electronic blood pressure measuring device of the present invention;

FIGS. 19a and b are wave form diagrams for showing the differentiated pulse wave wave form and the pulse wave wave form for illustrating the division of the pulse wave in said second preferred embodiment electronic blood pressure measuring device, and:

DESCRIPTION OF THE PREFERRED EMBODIMENTS

Figure 1:
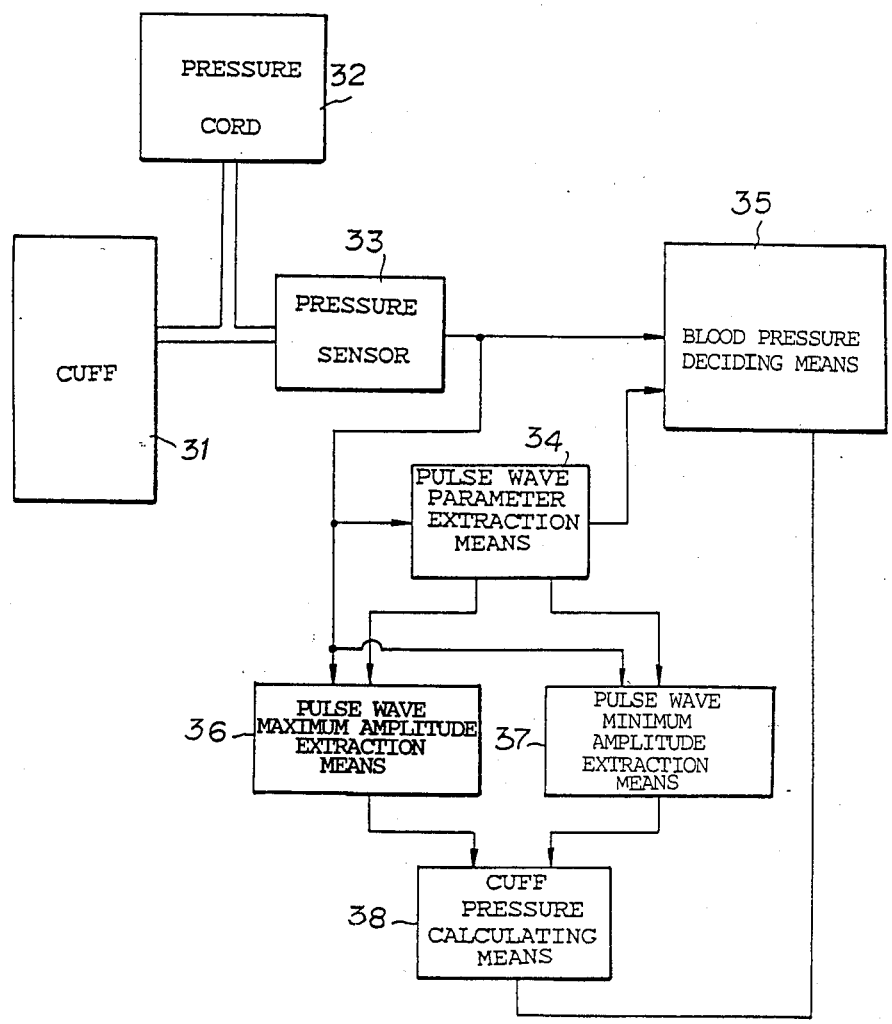
FIG. 1 is a block diagram showing the schematic structure of the first preferred embodiment of the electronic blood pressure measuring device of the present invention.
Figure 2:
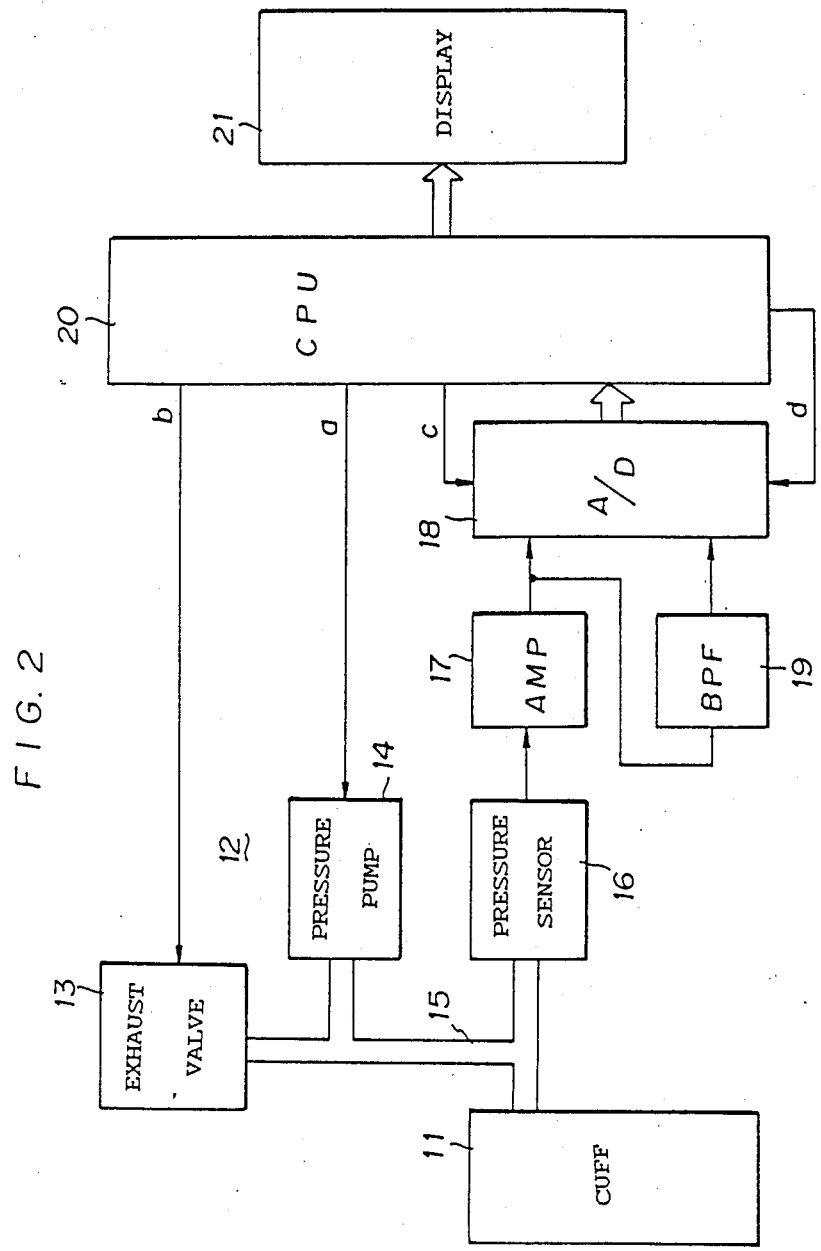
FIG. 2 is another block diagram relating to said first preferred embodiment of the electronic blood pressure measuring device of the present invention.

The present invention will now be described with reference to the preferred embodiments thereof. FIG. 1 is a block diagram showing the schematic structure of the first preferred embodiment of the electronic blood pressure measuring device of the present invention, and FIG. 2 is a block diagram of an electronic blood pressure measuring device to which this invention is applied. In FIG. 1, cuff 31 is formed as a bag or the like to be applied to the arm of a patient, which can be made of rubber of some other suitable flexible material. Cuff 31 is connected to a pressure cord 32. A pressure sensor 33 is connected to cuff 31 by way of a rubber tube or the like and converts the cuff pressure sense thereby into an electric signal. The output of pressure sensor 33 is connected to the input of blood pressure deciding means 35 as well as to pulse wave maximum amplitude extraction means 36 and pulse wave parameter extraction means 34. Outputs from pulse wave parameter extraction means 34 are supplied to blood pressure deciding means 35, pulse wave maximum amplitude extraction means 36 and pulse wave minimum amplitude extraction means 37. Cuff pressure calculating means 38 receives the outputs from pulse wave maximum amplitude extraction means 36 and pulse wave minimum amplitude extraction means 37 and passes blood pressure values along to blood pressure deciding means 35. FIGS. 2-5 describe more completely the aspects of the first preferred embodiment of this invention. In FIG. 2, a cuff 11 is formed as a bag, which may be made of rubber or of some other suitable material, for being wound upon the arm of a patient or of some other person the blood pressure of whom is desired to be measured, and this cuff 11 is connected to an exhaust valve 13 and to a pressurization pump 14 which together make up a pressure system 12, by way of a rubber tube 15. A pressure sensor 16 is connected to the cuff 11 by way of the rubber tube 15 and converts the current value of the cuff pressure into an electric signal. The output end of the pressure sensor 16 is connected to an input end of an amplifier 17 and the output electric signal of the pressure sensor 16 or the cuff pressure signal is DC amplified by the amplifier 17. The output end of the amplifier 17 is connected to an input end of an A/D converter 18 on the one hand and is connected to an input end of a band pass filter 19 on the other hand. The output end of the A/D converter 18 is fed to a CPU 20, as is the output of the band pass filter 19, so that the output of the amplifier 17 and the output of the band pass filter 19 are supplied to the CPU 20 after being converted into digital signals by the A/D converter 18.

The CPU 20, which performs certain processes according to an internal program, has the functions of determining the blood pressure values such as the maximum blood pressure and the minimum blood pressure, and the determined blood pressure values are displayed on a display unit 21.

As a measurement start key which is not shown in the drawing is actuated, the CPU 20 starts the action of the pessurization pump 14 and pressurizes the cuff 11 by a command "a" and controls the amount of air exhaustion from the exhaust valve 13 by a command "b". And the cuff pressure from the amplifier 17 and the pulse wave component from the band pass filter 19 are read out at a certain sampling timing by commands "c" and "d".

The CPU 20 has the functions of detecting the maximum value and the minimum value of the pulse wave component read out in a certain time interval which is longer than the above mentioned sampling timing time, computing the level difference between the maximum value and the minimum value, extracting cuff pressures corresponding to the maximum value and the minimum value, and computing the average value of these extracted cuff pressures.

Figure 3:
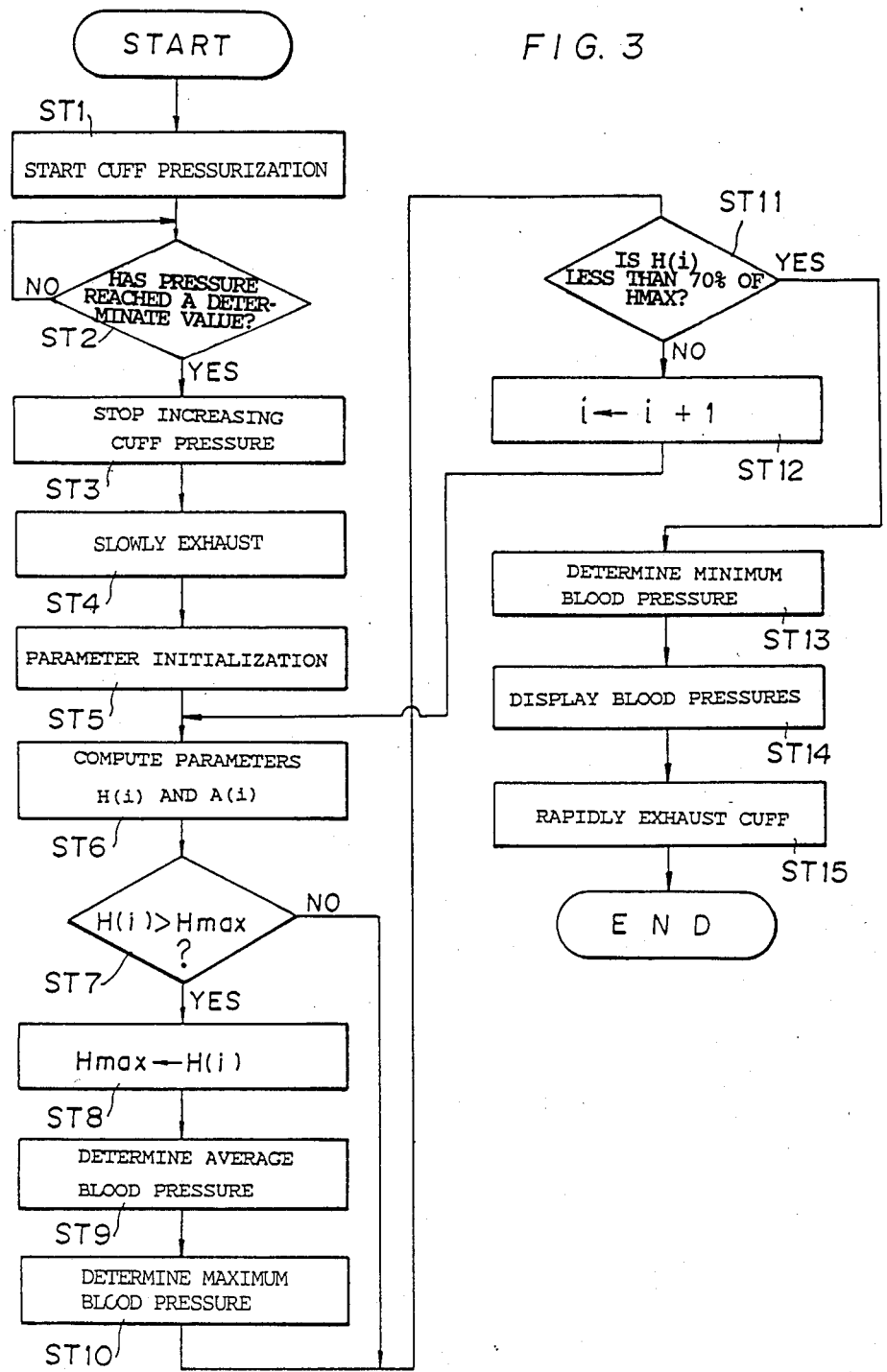
FIG. 3 is a flow diagram showing the overall operation of a main program for a microprocessor incorporated in said first preferred embodiment electronic blood pressure measuring device.

Now, the overall action of the electronic blood pressure measuring device of this embodiment will be described with reference to a flow diagram of the program therefor shown in FIG. 3.

As the action starts by the measurement start key which is not shown in the drawing being pressed, the pressure pump 14 starts its action on receiving the command "a" from the CPU 20 (in the step ST1), and the cuff 11 is pressurized until a cuff pressure which is sufficient for measurement builds up (in the step ST2). And when the cuff pressure reaches a certain cuff pressure value, the action of the cuff pressure pump 14 stops to terminate the pressurization (in the step ST3), and by the command "b" the exhaust valve 13 starts gradual exhaustion of air in the cuff 11 so as to start depressurization of said cuff 11 (in the step ST4). And various computing parameter initialization stages are conducted, such as for example clearing the counter for computing the parameters and the registers for storing the maximum values and the minimum values of the cuff pressure and so on (in the step ST5). Then, the parameters are computed (in the step ST6). In this parameter computing process, the maximum value Pmax and the minimum value Pmin of the pulse wave component read out in the finely divided sampling time intervals (windows) are derived and the parameter value H(i) for each samplimg time interval is derived as the difference between the maximum value Pmax and the minimum value Pmin. And, in this process, the cuff pressure A(i) for each sampling time interval is also extracted. This computing process is a characteristic of this invention, and its details are described hereinafter.

After this computing process, currently the computed parameter H(i) and the parameter maximum value Hmax up to that time point are compared (in the step ST7), and if H(i) is greater than Hmax the current parameter H(i) is stored as a new parameter maximum value Hmax (in the step ST8) to determine the cuff pressure at that time point as the average blood pressure (in the step ST9). And then, the cuff pressure corresponding to the parameter value which corresponds for instance to one half of the parameter maximum value Hmax is set as the maximum blood pressure (in the step ST10).

And then it is determined whether the current parameter value H(i) is equal to or less than 70% of the parameter maximum value Hmax up to that point or not (in the step ST11). If the parameter is rising, this determination result will be NO, and after the interval counter i is incremented by 1 (in the step ST12) the system flow returns to the step ST6 to compute the parameter for the next time interval. Thereafter, until the parameter value stops rising and starts dropping, and becomes 70% of Hmax, the processes in the steps ST6 to ST12 are repeated. As the parameter H(i) reaches 70% of Hmax and diminishes further, the determination result of the step ST11 becomes YES and the cuff pressure corresponding to this time point is determined as the minimum blood pressure (in the step ST13). And then the blood pressure values determined as average, maximum, and minimum are displayed on the display unit 21 (in the step ST14), and the exhaust valve 13 starts rapid exhaustion (in the step ST15), to complete the measurement.

Figure 4:
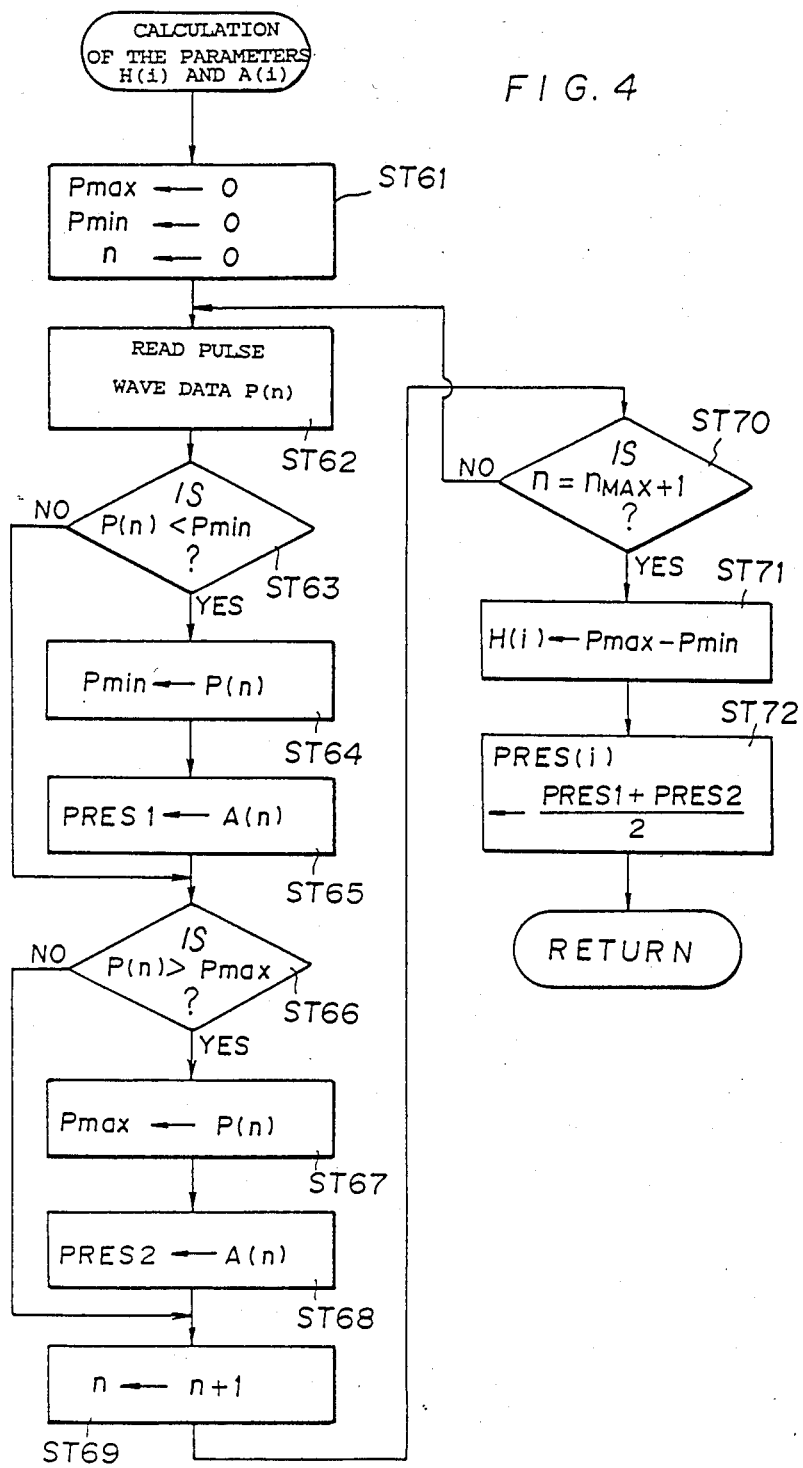
FIG. 4 is a flow diagram showing in greater detail the control flow of a parameter computing routine which is invoked from said main program.

Now, the details of the computing process for the parameters H(i) and A(i) in the step ST6 mentioned above, which may be performed by a subroutine which is invoked, will be described in the following with reference to the subroutine flow diagram shown in FIG. 4.

As the system flow enters the subroutine for computing these parameters, first of all in the step ST61 the registers for storing the maximum pressure Pmax and the minimum value Pmin of the pulse wave component levels and the number of sampling n in each interval are cleared. And the pulse wave component levels P(n) entered for each sampling time are read (in the step ST62). And the pulse wave component levels P(n) which are read are compared with the minimum value Pmin of the pulse wave component level up to that point (in the step ST63), and if P(n) is smaller then the P(n) of the current sampling time is stored as Pmin (in the step ST64). And the cuff pressure A(n) at this time point is stored as PRES1 (in the step ST65). This PRES1 is a cuff pressure corresponding to the minimum value of the pulse wave. In the step ST63, if P(n) is greater than Pmin, the processes performed by the steps ST64 and ST65 are skipped. In the steps ST63 to ST65, minimum value of the pulse wave level is updated.

After this updating process for the minimum value, in the step ST63, P(n) is compared with the maximum value Pmax up to that point, and if P(n) is greater then the P(n) of the current sampling is stored as Pmax (in the step ST67). And cuff pressure A(n) at this time point is stored as PRES2 (in the step ST68). This PRES2 is a cuff pressure corresponding to the maximum value of the pulse wave. If P(n) is less than Pmax in the step ST66, the processes performed in the steps ST67 and 68 are skipped. In the steps ST66 and ST68, the maximum value of the pulse wave level is updated.

After the number of detections n is incremented by 1 (in the step ST69), it is determined whether this detection number n has exceeded a maximum detection number nmax of the interval or not (in the step ST70). If not, the system flow returns to the step ST62 and after reading the data P(n) of the pulse wave level for te next sampling time the same steps (i.e. the samesteps ST62 through ST70) are executed again. These processes are repeated until n is equal to nmax+1 or one time interval is completed.

When n is equal to nmax+1, the determination result of the step ST70 becomes YES. Then, the mimimum value of the pulse wave is subtracted from the maximum value Pmax of the pulse wave, and the difference or the parameter H(i) is computed (in the step ST71) on the one hand, and the average value of the cuff pressures PRES1 and PRES2 corresponding to the maximum and the mimimum values of the pulse wave is computed, and after this average value is set as the cuff pressure PRES(i) of this time interval the system flow returns to the main routine (in the step ST72).

The computing processes for the parameter H(i) and the corresponding cuff pressure A(i) will now be further described with reference to the wave form examples shown in FIG. 5.

Figure 5:
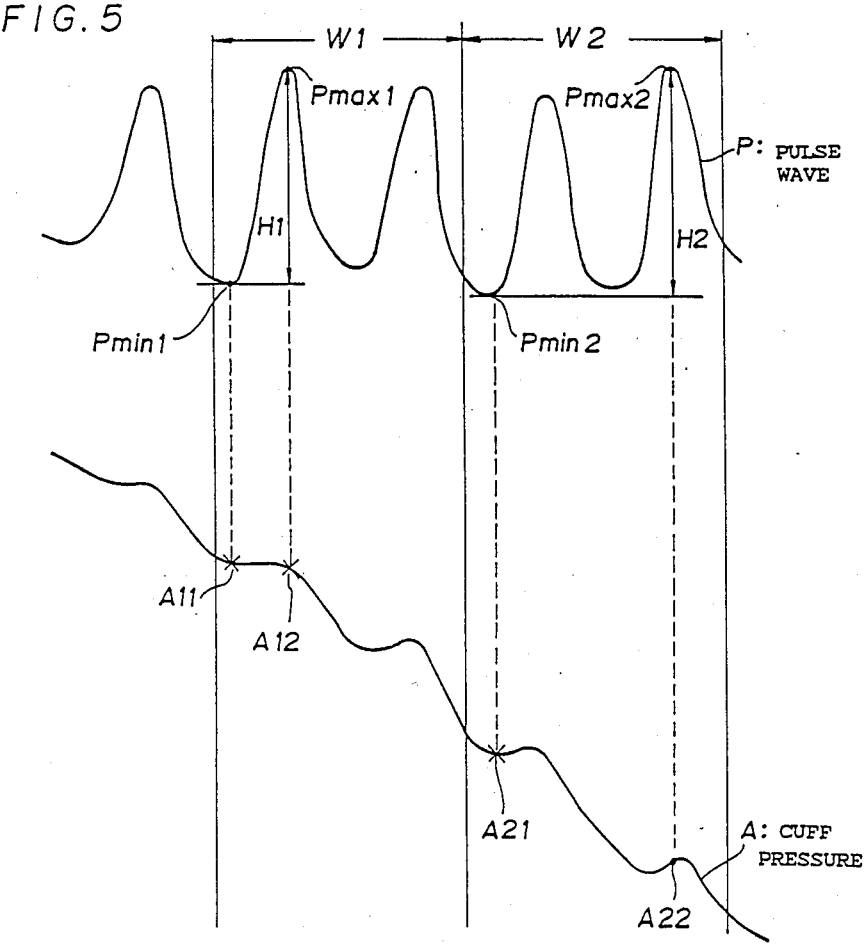
FIG. 5 is a diagram showing the relation between the pulse wave component and the cuff pressure curve for illustrating the action of this first preferred embodiment electronic blood pressure measuring device.
Figure 6:
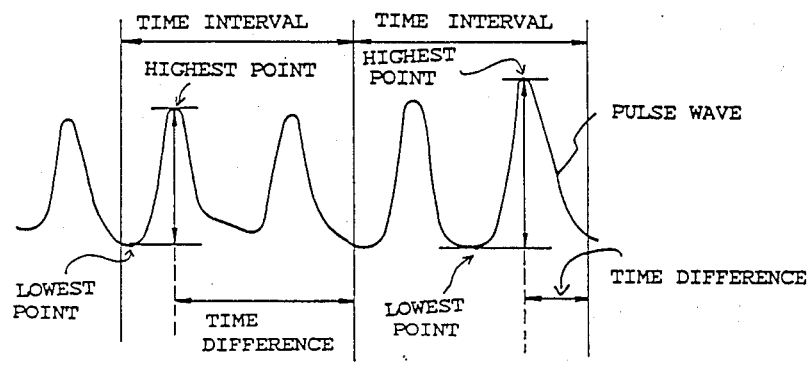
FIG. 6 is a diagram for showing the problems of a conventional electronic blood pressure measuring device.
Figure 7A:
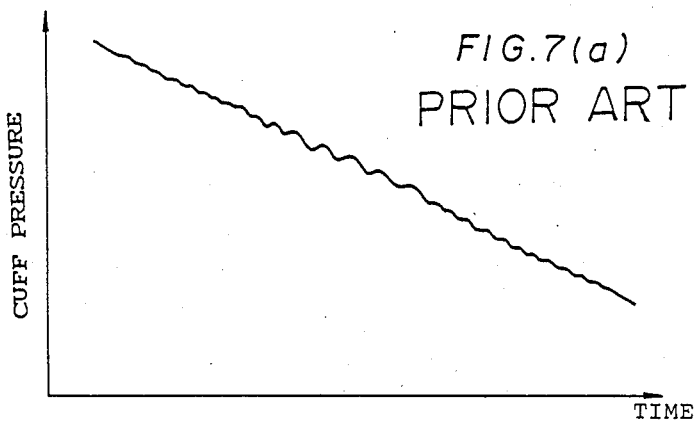
FIGS. 7a to 7c are diagrams showing the principle of a prior art type electronic blood pressure measuring device which is based upon the oscillation method which computes a parameter for each time interval.
Figure 7B:
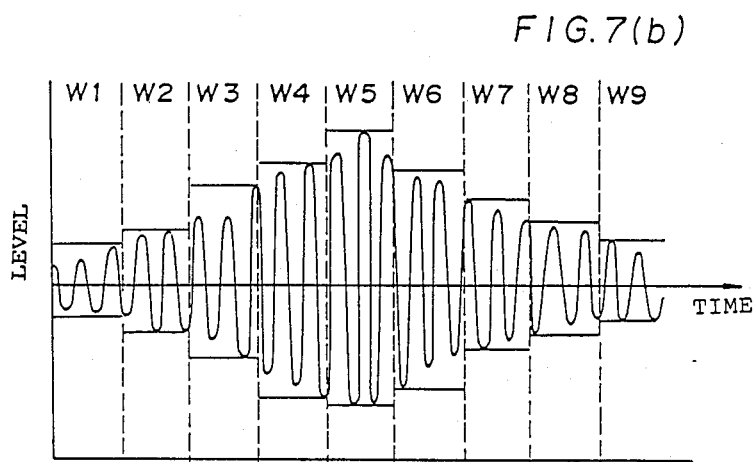
Figure 7C:
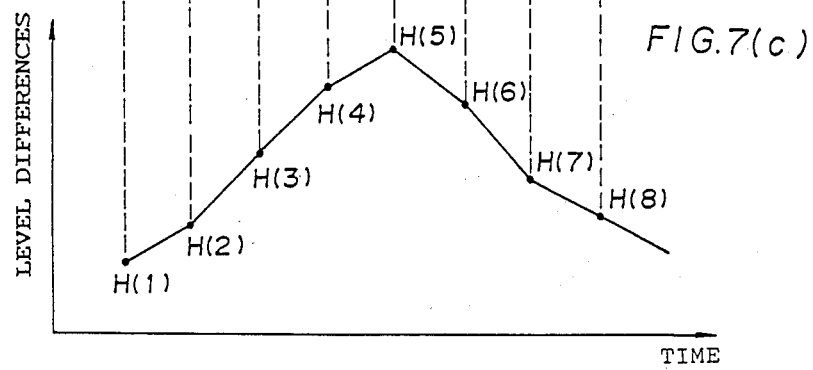

In FIG. 5, "p" denotes a pulse wave component and "a" denotes a cuff pressure wave form. W1, W2, and so on are time intervals. With respect to the time interval W1, from the cuff pressure A11 corresponding to the mimimum value of the pulse wave Pmin1 and the cuff pressure A12 corresponding to the maximum value of the pulse wave Pmax1, the corresponding cuff pressure of this interval W1 is A1=(A11+A12)//2. With respect to the time interval W2, from the cuff pressure A21 corresponding to the minimum value of the pulse wave Pmin2 and the cuff pressure A22 corresponding to the maximum value of the pulse wave Pmax2, the corresponding cuff pressure of this time interval W2 is A2=(A21+A22)/2. Therefore, even when there are some fluctuations in the maximum and mimimum values of the pulse wave for different time intervals, the cuff pressures close to the points where the minimum and the maximum values are extracted are determined as the cuff pressure of the corresponding intervals.

Thus, according to this invention, since the average values of the cuff pressures corresponding to the maximum and the minimum values of the pulse wave component in each of the time intervals for obtaining the parameters are set as the cuff pressures of the corresponding time intervals, a non distorted relationship is obtained between the parameters and the cuff pressures, and an electronic blood pressure measuring device which operates with very little error and with very high precision can be obtained.

Figure 8A:
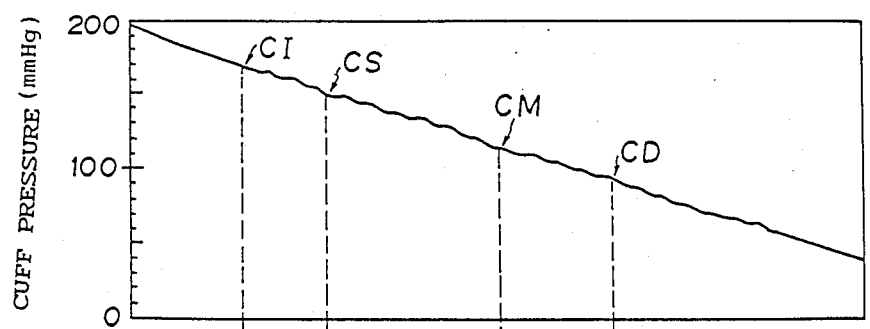
FIG. 8a is a drawing showing the process of depressurizing the cuff pressure.
Figure 8B:
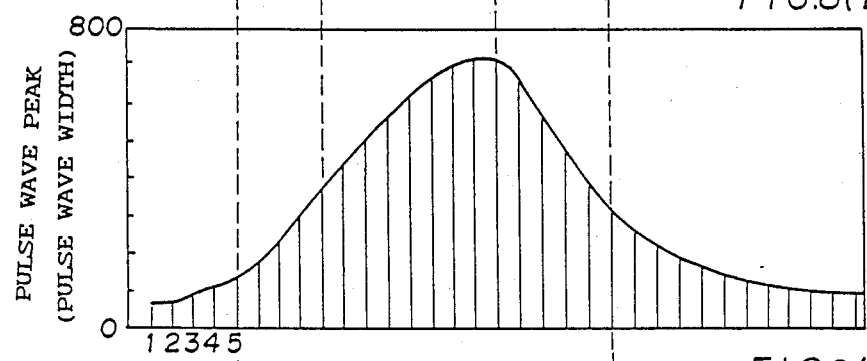
FIG. 8b is a drawing showing a series of pulse wave peaks during the depressurization process.
Figure 8C:
FIG. 8c is a drawing showing the distribution of the partial areas surrounded by the envelope line and the straight line portion of the pulse wave peaks in time series.
Figure 9:
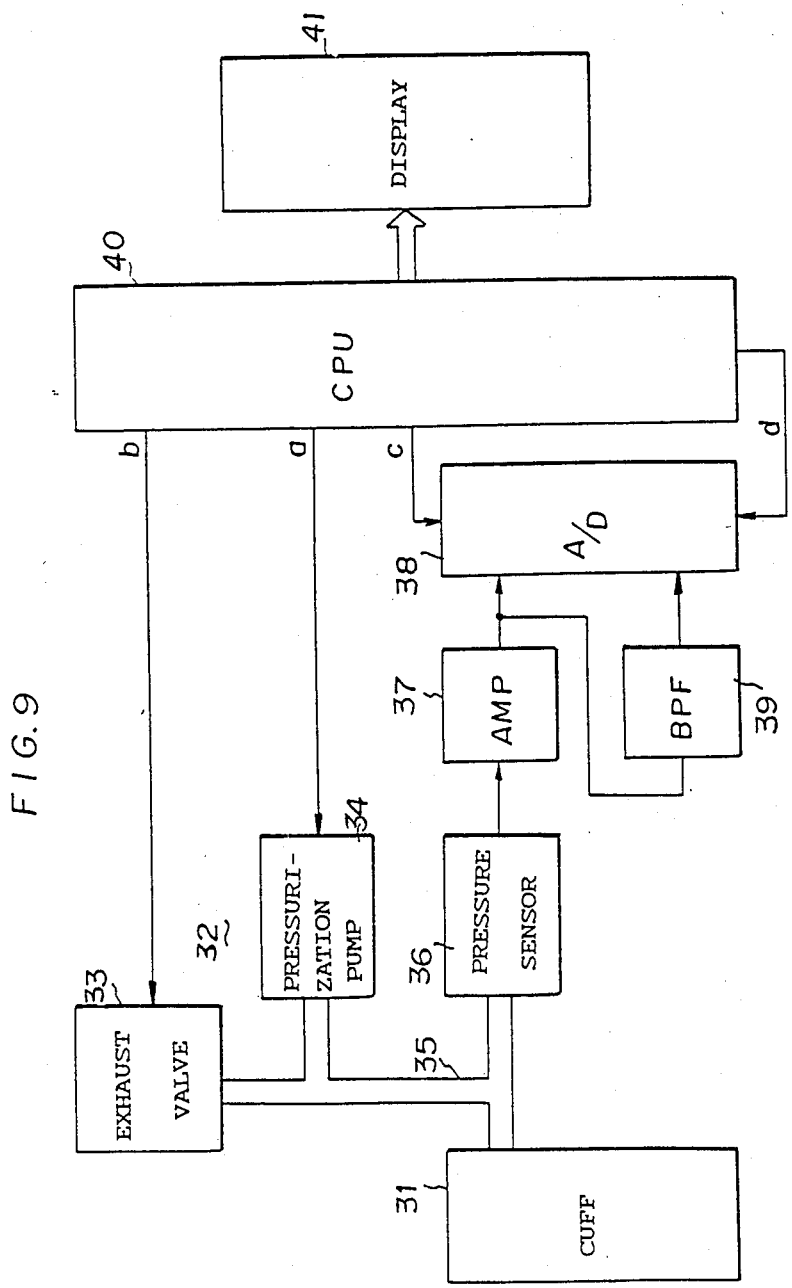
FIG. 9 is a block diagram of said second preferred embodiment of the electronic blood pressure measuring device of the present invention.
Figure 10:
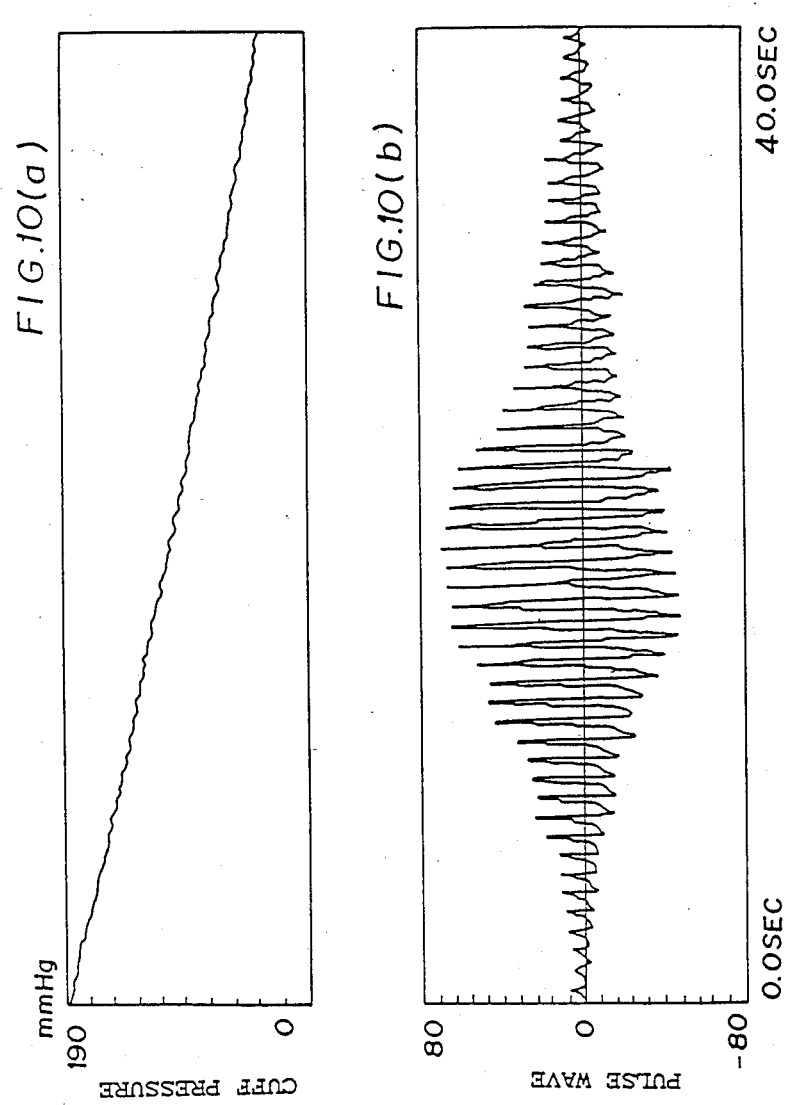
FIGS. 10a and 10b are drawings showing the changes in the cuff pressure and the pulse wave amplitude during the depressurization of the cuff pressure in this second preferred embodiment electronic blood pressure measuring device.
Figure 11:
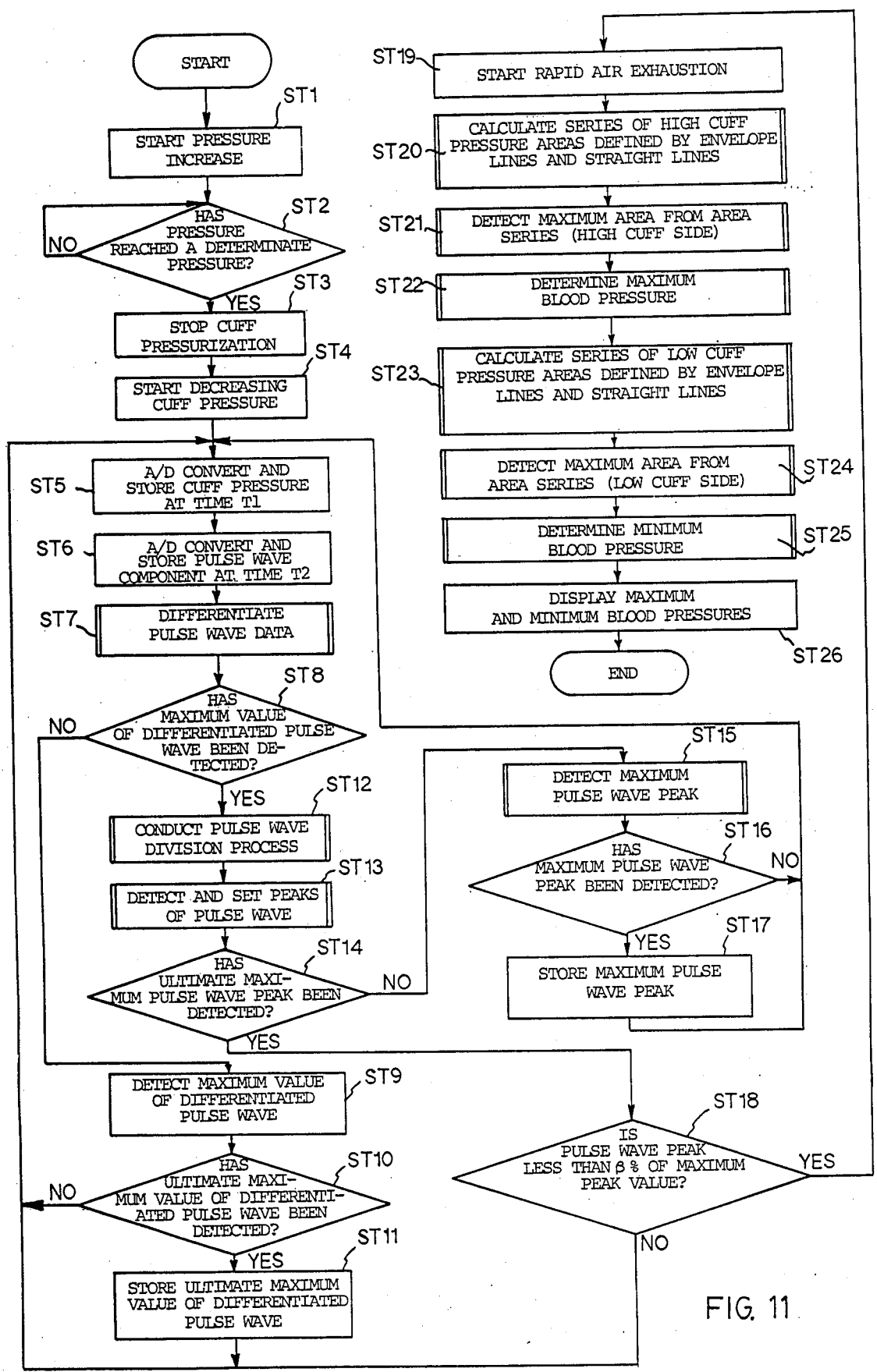
FIG. 11 is a flow diagram showing the overall operation of a main program for a microprocessor incorporated in said second preferred embodiment electronic blood pressure measuring device.

FIG. 9 is a block diagram of an electronic blood pressure measuring device which is a second preferred embodiment of the electronic blood pressure measuring device of the present invention. (Reference numerals in FIGS. 8 through 20 for this second preferred embodiment do not particularly correspond to reference numerals relating to FIGS. 1 through 7 for the first preferred embodiment). In FIG. 9, a cuff 1 is formed as a bag to be wound on the arm of a patient, being as before made of rubber or of some other suitable flexible material, and this cuff 1 is connected to a pressure system 2 comprising an exhaust valve 3 and a pressurization pump 4 by way of a branched rubber tube 5. A pressure sensor 6 is connected to the cuff 1 by way of the rubber tube 5 and converts the cuff pressure sensed thereby into an electric signal. The output of the pressure sensor 6 is connected to an input end of an amplifier 7, and the output electric signal of the pressure sensor 6 or the cuff pressure signal is DC amplified by the amplifier 7. The output end of the amplifier 7 is connected to an input end of an A/D converter 8 on the one hand, and to an input end of a band pass filter 9 on the other hand. The output end of the A/D converter 8 is connected to a CPU 10, and so is the output of the band pass filter 9; and thereby the output of the amplifier 7 and the output of the band pass filter 9 are both supplied to the CPU 10 after being converted into digital signals by the A/D converter 8.

The CPU 10 executes predetermined processes according to an internal program stored therein, and has the functions of determining the blood pressure values such as the maximum blood pressure, the minimum blood pressure, and so on, and determined blood pressure values are displayed on a display unit 11.

When a measurement start key which is not particularly shown in the drawing is actuated, the CPU 10 starts the action of the pressurization pump 4 to pressurize the cuff 1 by issuing a command "a", and controls the air exhaust from the exhaust valve 3 by issuing a command "b". And the cuff pressure from the amplifier 7 and the pulse wave component from the band pass filter 9 are read in at certain sampling cycles by commands "c" and "d". According to this electronic blood pressure measuring device, after the cuff 11 is wound around the arm of the patient; and the pessurization pump 4 is actuated by operating the measurement start key until the cuff pressure reaches a certain level, the pressurization pump 4 is stopped and the air exhaust is gradually started by the exhaust valve 3. As the cuff pressure gradually drops, the output signal of the pressure sensor 6 becomes as shown in FIG. 3a and the extracted pulse wave component from the output of the band pass filter 9 or the output from the amplifier 7 becomes as shown in FIG. 3b.

The CPU 10 determines the average blood pressure, the maximum blood pressure, and the minimum blood pressure from the detected cuff pressure and the amplitude value of the pulse wave (peak value) according to a flow which will be described hereinafter. Now, this action will be described with reference to the flow chart of FIG. 4.

First of all, when the measurement start key is pressed and the action is started, the pressurization pump 4 starts its action by the command "a" (in the step ST1), and the cuff 1 is pressurized until a determinate pressure sufficient for measurement is built up (in the step ST2). And, when the cuff pressure reaches a certain predetermined cuff pressure, the action of the pressurization pump 4 is stopped and at the same time as stopping the pressurization (in the step ST3) the exhaust valve 3 begins gradual air exhaustion by the command "b" to begin depressurization (in the step ST4). And by the command "c", for every T1 (for instance 100 ms as an example) the output of the amplifier 7 or the cuff pressure is A/D converted and is stored (in the step ST5). Likewise, by a command, for each T2 (for instance 10 ms in the same example) the output of the band pass filter 9 or the pulse wave component is A/D converted by the A/D converter 8 and is taken in by the CPU and is stored (in the step ST6).

The discrete data of the pulse wave which has been A/D converted is differentiated for each point (in the step ST7). This differentiation is conducted according to the following equation:

$$f'(n) = \frac{\sum_{j=1}^{m} \{f(n+j) - f(n-j)\} \times j}{k}$$

where n=1, 2, 3 and so on, k is a normalization constant (k=110 in the illustrative example), and f(n) is an original data with n selected as 5 in the example.

FIG. 18 shows the wave forms of the pulse wave before and after the differentiation. FIG. 18a is a differentiated wave form, and FIG. 18b is the pulse wave wave form.

Then the maximum value of the differentiated pulse wave is extracted. Specifically, following the differentiation process in the step ST7, it is determined whether the maximum value of the differentiated pulse wave has been detected or not (in the step ST8), and this detection of the maximum value of the differentiated pulse wave is repeated until such a value is detected (in the step ST9). This process consists of comparing the current differentiated value and the maximum value up to the point and renewing or updating the maximum value if the current value is greater than the previous maximum value, and if the value is not updated for more than a certain time interval (for instance three seconds) the value is considered as the maximum value of the differentiated pulse wave.

Therefore, when the certain time interval has elapsed without the differentiated value being updated, the determination result for the detection of the maximum value of the differentiated pulse wave in the step ST10 is NO, and the process flow returns to the step ST5 and the process of detecting the maximum value of the differentiated pulse wave is repeated on a real time basis. When the maximum value of the differentiated pulse wave is detected, the determination result of the step ST10 becomes YES, and the maximum value of the differentiated pulse wave is stored (in the step ST11). And the process flow returns to the step ST5, but since the determination result for the detection of the maximum value of the differentiated pulse wave in the step ST8 now becomes YES, the process flow moves on to the step ST12 and conducts a pulse wave division process.

This pulse wave division process consists of setting $\alpha$ percent ($\alpha$ is equal to 10 to 20) of the maximum value of the differentiated pulse wave extracted in the step ST9 as a threshold level, finding an intersecting point between this level and the rising curve of the differentiated pulse wave, and setting the point on the pulse wave wave form corresponding to this intersecting point as a division point. The line TH shown in FIG. 19 is the threshold level, and d1, d2, d3 and so on are division points.

And the maximum value of the pulse wave is detected for each of the intervals defined by this division of the pulse wave (in the step ST13), and these maximum values of the pulse wave are set as the pulse wave peaks. And the maximum value of these pulse wave peaks are obtained for various division intervals. The detection of the maximum peak value of the pulse wave consists of comparing the current pulse wave peak value to the preceding pulse wave peak values, and if the current pulse wave peak value is greater than the previous ones the greater pulse wave is stored as updating data, and if no updating takes place for more than a certain time interval the pulse wave peak value is stored as the maximum peak value of the pulse wave (in the step ST17). The cuff pressure corresponding to this maximum peak value of the pulse wave is stored as an average blood pressure CM.

When the maximum peak value of the pulse wave is stored, the determination result on the detection of the maximum peak value of the pulse wave in the step ST14 becomes YES, and then it is determined whether or not the pulse wave peak value is equal to or less than $\beta$ percent ($\beta$ is equal to 40 to 60%) of the maximum peak value (in the step ST18). If it is not equal to or less than $\beta\%$, the process flow returns to the step ST5 and the processes including the cuff pressure A/D conversion, storage (in the step ST5), pulse wave A/D conversion, storage (in the step ST6), the pulse wave peak detection (in the step ST14) and so on are repeated.

When the pulse wave peak becomes equal to or less than $\beta\%$ of the maximum peak, the determination result of the step ST18 becomes YES, meaning that the pulse wave peak value which is necessary for measurement has already been measured in this state, and a command "b" is outputted from the CPU 10 to the exhaust valve 3. As a result, the exhaust valve 3 starts rapid air exhaustion (in the step ST19).

Thus, the real time processes such as differentiation of the pulse wave, detection of pulse wave peaks, and so on in the depressurization process of the cuff pressure are completed. Thereafter, certain processes are executed on the pulse wave peak values obtained in this real time process, and subsequent thereto the process of determining the maximum blood pressure and the minimum blood pressure is to be started. Now, the process of determining blood pressures will be described in the following.

After rapid air exhaustion, a row of areas (a(n)) defined by the envelope lines and the straight lines are computed with respect to the group of data of the extracted pulse wave peaks (PP(n)) on the higher cuff pressure side of the pulse wave maximum peak (Pmax) (in the step ST20).

A concrete example of the computations of the areas a(n) will be described in the following with reference to FIG. 20.

Figure 20:
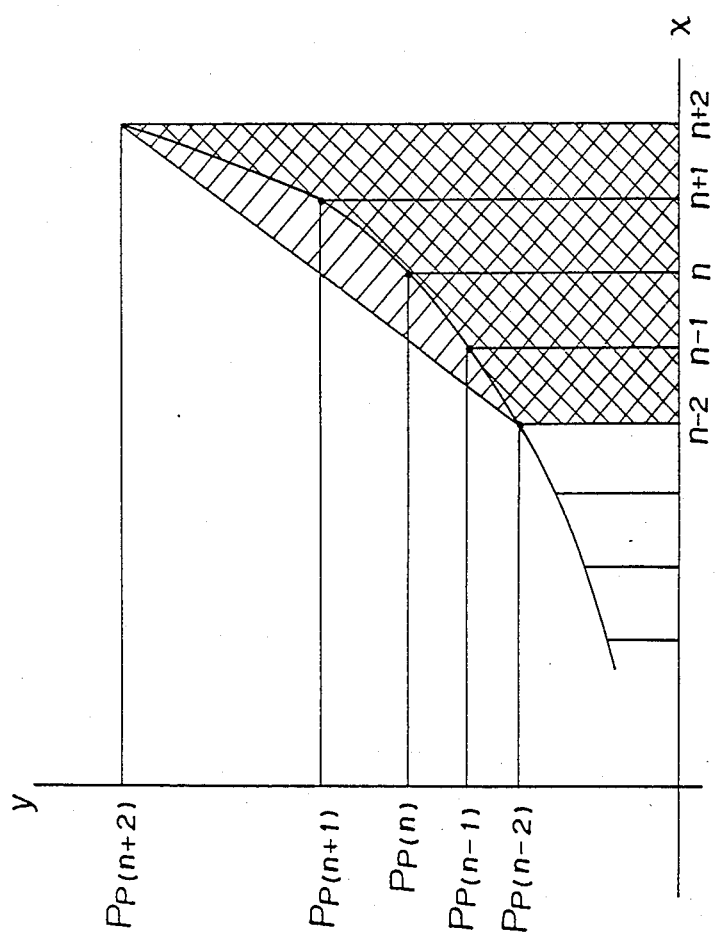
FIGS. 20 is a drawing for showing the derivation of the partial areas in the higher cuff pressure side in said second preferred embodiment electronic blood pressure measuring device.

In FIG. 20, n on the x axis denotes pulse wave serial numbers, while the y axis represents corresponding pulse wave peaks. The area a(n) represented by the pulse wave number n is obtained by subtracting an area defined by points (n−2,0), (n+2,Pp(n+2)), (n−1,Pp(n−1)), (n,Pp(n)), (n+1,Pp(n+1), (n+2,Pp(n+2)), (n+2,0) from a trapezoidal area defined by points (n−2,0), (n−2,Pp(n−2)), (n+2,Pp(n−2), and (n+2,0).

The trapezoidal area defined by points (n−2,0), (n−2,Pp(n−2)), (n+2,Pp(n−2), and (n+2,0) is found as $\frac{1}{2}.4h(Pp(n+2)+Pp(n-2))$ if the interval h is between a point (i,0) and a point (i+1,0) where i is from n−2 to n+1).

Meanwhile the trapezoidal area Q(i) defined by the points (i,0), (i,pPi)), (i+1,Pp(i+1), and (i+1,0) (where i is from n−2 to n+1) is $Q(i) = \frac{1}{2}h(Pp(i)+Pp(i+1))$. Therefore, the area a(n) can be expressed by:

$$a(n) = \frac{1}{2} 4h(Pp(n+2) + Pp(n-2)) - \sum_{i=n-2}^{n+1} Q(i)$$

$$= \frac{1}{2} h [4(Pp(n+2) + Pp(n-2)) - \{Pp(n-2) + Pp(n-1)) + (Pp(n-1) + Pp(n)) + (Pp(n) + Pp(n+1)) + (Pp(n+1) + Pp(n+2))\}]$$

$$= \frac{1}{2} h \{3(Pp(n+2) + Pp(n-2)) - 2(Pp(n-1) + Pp(n) + Pp(n+1))\}$$

If $h = 1$, then $a(n)$ can be derived as:

-continued $$a(n) = \frac{3}{2} \{Pp(n+2) + Pp(n-2) - (Pp(n-1) + Pp(n) + Pp(n+1))\}$$

However, if any one of the points (n−1,Pp(n−1)), (n,Pp(n)), and (n+1,Pp(n+1)) is above a line connecting the points (n+2,Pp(n+2)) and (n−2,Pp(n−2)), since it means that the envelope line is within the range of the average blood pressure away from the area corresponding to the maximum blood pressure, a(n) is set as zero.

These areas a(n) are computed for each of the pulse wave numbers by incrementing the pulse wave number n for the pulse wave peaks shown in FIG. 8b by 1. And a row or series of areas (a(n)) are computed as shown in FIG. 8c.

Subsequently, a maximum area is detected from the area series (a(n)) (in the step ST21), and setting the cuff pressure value corresponding to the group of the pulse wave series which gives the maximum area value as CI (refer to FIG. 1) the maximum blood pressure value CS is determined from the following equation according to the average blood pressure value CM which has already been extracted and stored (refer to FIG. 1) (in the step ST22):

$$CS = \frac{1}{3}(CI - CM) + CM$$

The maximum blood pressure determined from this equation has been experimentally confirmed to be proper and practical.

Next, a series of areas a(n) surrounded by the envelope line and the straight lines are computed in the same way as in the step ST20 with respect to a series of data of the extracted pulse wave peaks PP(n) on the lower cuff pressure side of the pulse wave maximum peak (Pmax) (in the step ST23).

Subsequently, the maximum area is derived from the series of areas a(n), (refer to the right hand side of FIG. 8c) (in the step ST24), the minimum blood pressure value is determined from the cuff pressure value CD (refer to FIG. 8a) corresponding to the maximum value of the areas (in the step ST25). And, the maximum blood pressure and the minimum blood pressure are displayed on the display unit 11 (in the step ST26), and the measurement is completed.

Now, the specific processes in the subroutines invoked from the step ST20 to the step ST25 in the main flow will be described in the following.

Explanation of computation of the series of areas on the high cuff pressure side (in the step ST20).

Figure 12:
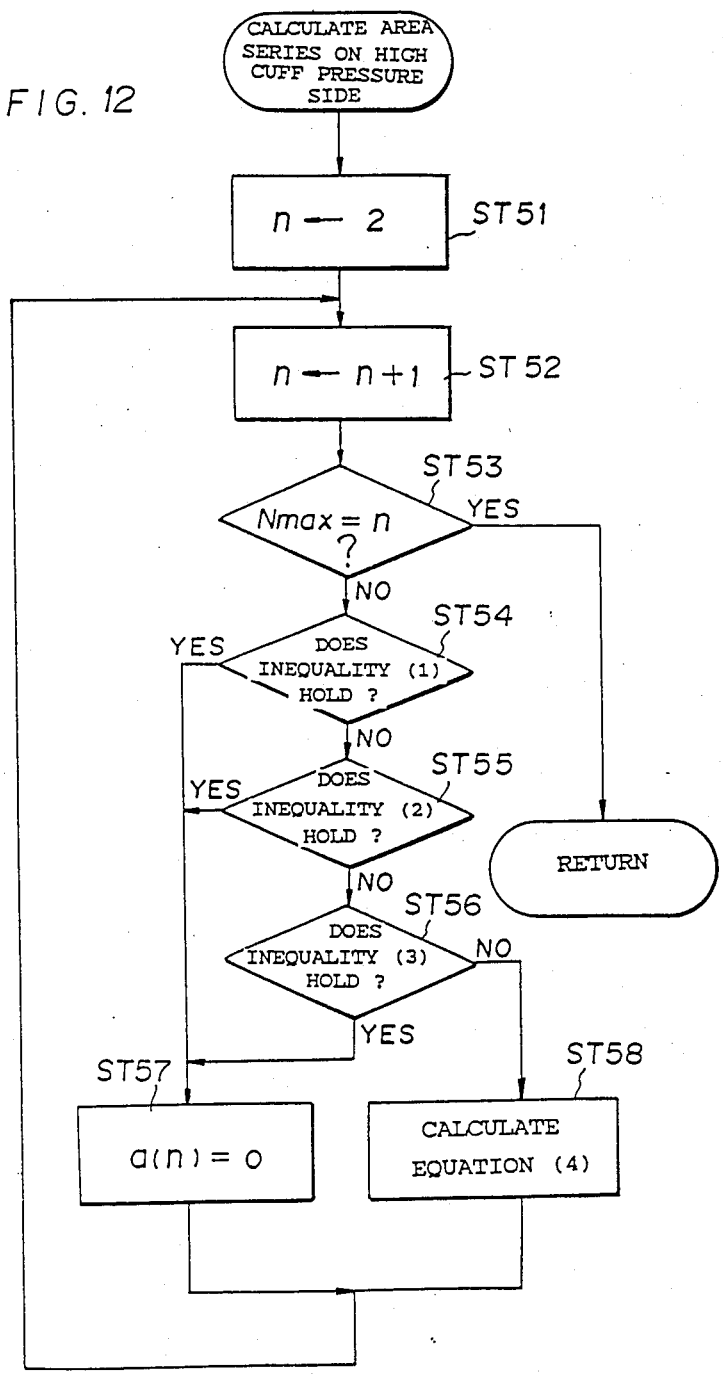
FIG. 12 is a flow diagram showing in greater detail the control flow of a routine, which is invoked from said main program, for the derivation of a series of areas on the higher cuff pressure side.

Upon entering the step ST20 in the main flow, the pulse wave number n is set to 2 (in the step ST51), as shown in the flow chart of FIG. 12, and 1 is added to n (in the step ST52), and it is determined whether or not nmax=n or not (in the step ST53). Here, nmax is an integer which causes Pmax to be equal to PP(nmax) (the cuff pressure corresponding to this nmax is the average blood pressure CM), and as long as the determination result is NO in the step ST53, the computation of the areas on the high cuff pressure side is to be executed. In other words, if the determination result of the step ST53 is NO, it is determined whether the following inequalities hold or not (in the step ST54, the step ST55, the step ST56):

$$Pp(n) > \frac{Pp(n-2) + Pp(n+2)}{2} \quad (1)$$

$$Pp(n-1) > \frac{\left(\left(\frac{Pp(n-2) + Pp(n+2)}{2}\right) + Pp(n-2)\right)}{2} \quad (2)$$

$$Pp(n+1) > \frac{\left(\left(\frac{Pp(n-2) + Pp(n+2)}{2}\right) + Pp(n+2)\right)}{2} \quad (3)$$

If any one of these inequalities holds, it means that either PP(n), PP(n−1), or PP(n+1) is located above the straight line previously identified, and therefore the area a(n) is determined as zero (in the step ST57). If none of the inequalities holds, then the equation:

$$a(n) = \frac{3}{2}(Pp(n+2) + Pp(n-2)) - \quad (4)$$

$$(Pp(n-1) + Pp(n) + Pp(n+1))$$

is executed (in the step ST58), and after the process flow has returned to the step ST52 n is incremented by one and the computation of the areas is repeated. In the step ST53, if nmax is equal to n, the computation of a(n) on the higher cuff pressure side is complete and the system flow returns to the main flow.

Explanation of computation of the maximum area on the high cuff pressure side (in the step ST21).

Figure 13:
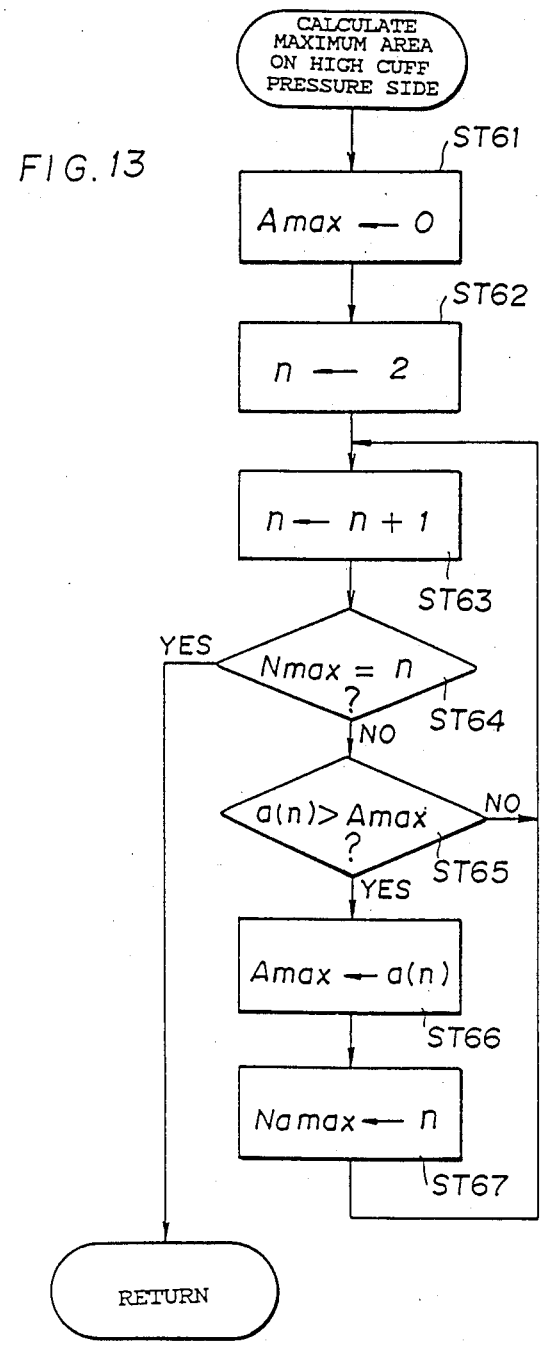
FIG. 13 is a flow diagram showing in greater detail the control flow of a routine, which is again invoked from said main program, for derivation of the maximum area values on the higher cuff pressure side.

Upon entering the step ST21 in the main flow, as shown in the flow chart of FIG. 13, the maximum value of the area Amax is set to zero (in the step ST61). And n is set to 2 (in the step ST62) and after unity is added to n (in the step ST63) it is determined whether or not nmax is equal to n or not (in the step ST64). And until this determination result becomes YES, the maximum value of the area amax is compared with the sequentially read out area values a(n) (in the step ST65), and if the read out area value a(n) is smaller than the maximum value the system flow returns as it is to the step ST63, but if the area value a(n) is greater than the maximum value this area value a(n) is used for updating the maximum area value amax (in the step ST66). And the value of n at this particular point is stored as nmax as being corresponding to the maximum area value amax (in the step ST67) and after the system flow has returned to the step ST63 n is incremented by unity to repeat the update process of the maximum area value amax thereafter. In the step ST64, if nmax is equal to n, the derivation of the maximum area on the high cuff pressure side is complete, and the system flow returns to the main flow.

Explanation of computation of the maximum blood pressure (in the step ST22).

Figure 14:
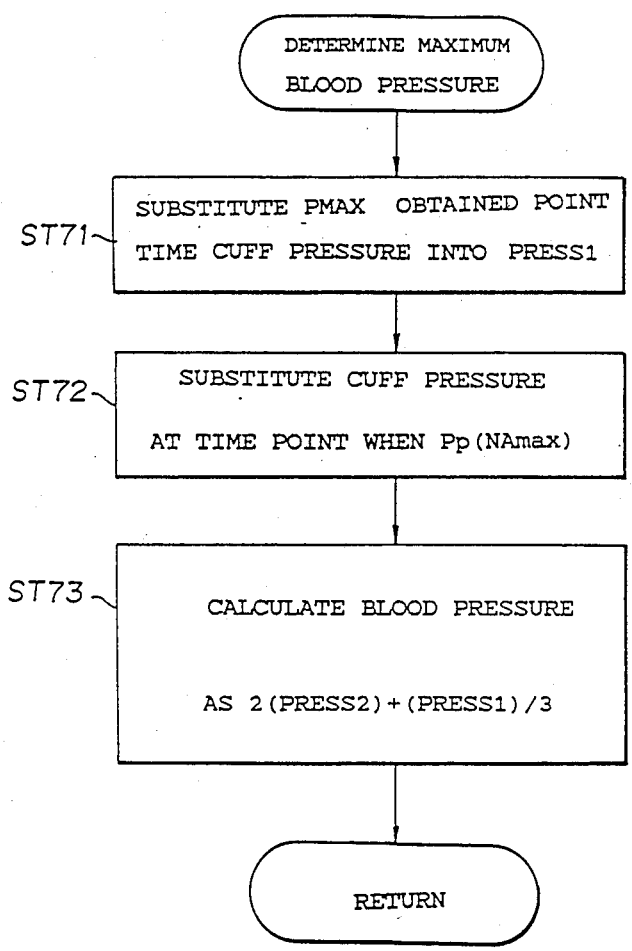
FIG. 14 is a flow diagram showing in greater detail the control flow of a routine, which is again invoked from said main program, for determination of the maximum blood pressure.

Upon entering the step ST22 in the main flow, as shown in the flow chart of FIG. 14, the cuff pressure CM at the time point when the maximum value Pmax of the pulse wave peak was obtained is substituted into PRESS1 (in the step ST71). Subsequently, the cuff pressure CI at the time point when the pulse wave peak Pp(Namax) maximizes the area is substituted into PRESS2 (in the step ST72). And by carrying out the computation (2(PRESS2)+(PRESS1)/3, the maximum blood pressure CS is determined (in the step ST73) before the system flow returns to the main flow.

Explanation of computation of the low cuff pressure side area (in the step ST23).

Figure 15:
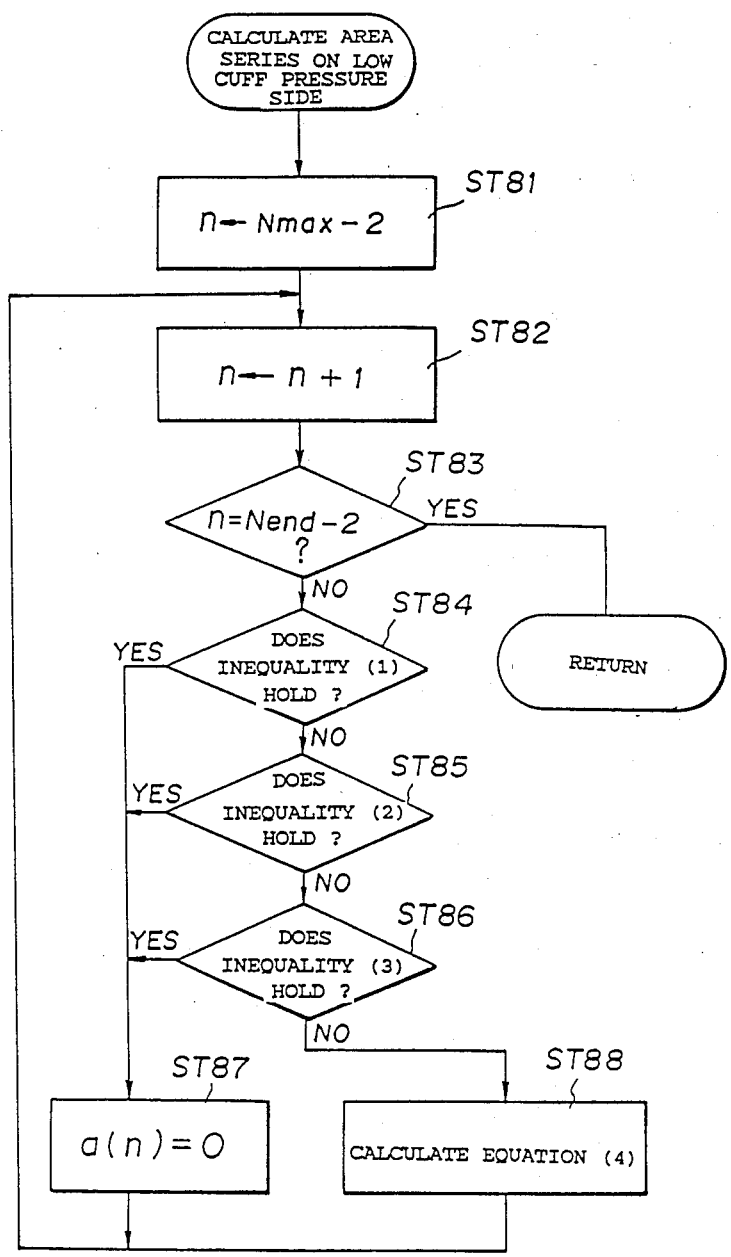
FIG. 15 is a flow diagram showing in greater detail the control flow of a routine, which is again invoked from said main program, for computation of the series of areas on the lower cuff pressure side.

Upon entering the step ST23 in the main flow, as shown in the flow chart of FIG. 15, first n is set to nmax−2 (in the step ST81), and after adding unity to n (in the step ST82) it is determined whether or not n is equal to nend−2 or not (in the step ST83). Here, nend is the serial number of the pulse wave which was extracted last of all. As long as the determination result of the step ST82 is NO, throughout the step ST84 to the step ST86, it is determined whether or not the same inequalities (1), (2), and (3) hold or not, in the same way as in the computation of the series of areas on the higher cuff pressure side described in connection with FIG. 12, and if either one of the inequalities holds a(n) is set to zero (in the step ST87), but on the other hand if none of the inequalities holds then the area a(n) is computed by equation (4) (in the step ST88) before the system flow returns to the step ST82. Thereafter, n is incremented by one in the step ST82, and the computation for the areas is repeated until n becomes equal to nend. In the step ST83, if n equals nend−2, the computation of the areas a(n) on the lower cuff pressure side is completed, and the system flow returns to the main flow.

Explanation of computation of the maximum area on the lower cuff pressure side (in the step ST24).

Upon entering the step ST24 in the main system flow, as shown in the flow chart of FIG. 16, first of all, the maximum value of the areas amax is set to zero (in the step ST91). And n is set to nmax−2 (in the step ST92), and after n is further incremented by one (in the step ST93) it is determined whether or not n is equal to nend−2 or not (in the step ST94). Until this determination result becomes YES, the area values a(n) and the maximum value of the areas amax are compared and the maximum value of the areas amax is updated (in the step ST95, and the step ST96) on the one hand, and the n at which an updating took place is stored as Namax (in the step ST97) before the system flow returns to the step ST93 on the other hand. Thereafter, the update process of the maximum area value amax is repeated. If n is equal to nend−2 in the step ST94, the derivation of the maximum area on the lower cuff pressure side is completed, and the system flow returns to the main flow.

Determination of the minimum blood pressure (in the step ST25)

Upon entering the step ST25 in the main flow, the cuff pressure CD at which the pulse wave peak Pp(Namax) which causes the minimum value of the areas is determined as the minimum blood pressure (in the step ST101). After this determination, this system flow returns to the main flow.

Thus, the various blood pressures can be measured from the cuff pressure and the pulse wave. It has been confirmed that the maximum, minimum, and the average blood pressures obtained according to the above described algorithm agree with the blood pressure measurements obtained by the use of Korotkoff sound.

Although in the above described embodiment a band pass filter was used to extract the pulse wave, according to this invention it is possible to use a digital filter instead, and it is also possible to feed the cuff pressure signal containing a pulse wave signal into a CPU and to separate the cuff pressure signal and the pulse wave component by a software process which is different from a digital filter.

Further, although in the above described second preferred embodiment extraction of the pulse wave peak values was conducted by pulse wave division after deriving the differentiated values of the pulse wave, the extraction of the pulse wave peak values is not to be considered as limited thereby, according to this invention.

Thus, according to the electronic blood pressure measuring device of this second preferred embodiment of the present invention, as opposed to conventional electronic blood pressure measuring devices, since a blood pressure measurement is conducted by making use of information on cuff pressure and the amplitude of the pulse wave which is an oscillation within the cuff pressure, and the frequency range of this pulse wave is as low as from 1 Hz to 10 Hz, by providing a filter of such a band, almost all the external noises and oscillation noises can be eliminated, so that the amplitude information of the pulse wave can be used for processing by arithmetic means without involving any distortion, and accurate blood pressure measurement is possible even in the environment filled with noise. In particular, since the determination of the blood pressure is based upon the computation of the areas surrounded by the envelope line of the pulse wave amplitude which does not contain noise components, and the line connecting both ends of a predetermined number of data to use these partial areas as parameters, the differences in the areas become very conspicuous, and therefore accurate measurement of blood pressure becomes possible.

Although the present invention has been shown and described in terms of certain preferred embodiments thereof, and with reference to the appended drawings, it should not be considered as being particularly limited thereby. The details of any particular embodiment, or of the drawings, could be varied without, in many cases, departing from the ambit of the present invention. Accordingly, the scope of the present invention is to be considered as being delimited, not by any particular perhaps entirely fortuitous details of the disclosed preferred embodiments, or of the drawings, but solely by the legitimate and properly interpreted scope of the accompanying claims, which follow.

What is claimed is:

1. An electronic blood pressure meter, comprising:
   (a) a cuff;
   (b) a pressure system coupled to said cuff for pressurizing and evacuating said cuff;
   (c) a pressure sensor coupled to said cuff for detecting the pressure within said cuff;
   (d) a pulse wave parameter extraction means which extracts the maximum level difference in the pulse wave component of the cuff pressure over a certain time interval, for each of a plurality of time intervals;
   (e) a blood pressure determining means for determining a blood pressure according to said cuff pressure and said pulse wave parameter;
   (f) a pulse wave maximum value corresponding cuff pressure extracting means for extracting the cuff pressure corresponding to the maximum value of the pulse wave component over each of said time intervals;
   (g) a pulse wave minimum value corresponding cuff pressure extracting means for extracting the cuff pressure corresponding to the minimum value of the pulse wave component over each of said time intervals; and (h) a cuff pressure averaging means for computing an average value of said cuff pressure extracted by said pulse wave maximum value corresponding cuff pressure extracting means and said cuff pressure extracted by said pulse wave minimum value corresponding cuff pressure extracting means;

(i) said average value as computed by said cuff pressure averaging means being taken as the cuff pressure of a particular time interval.

* * * * *